(12) United States Patent
Wiebe et al.

(10) Patent No.: US 11,103,750 B2
(45) Date of Patent: Aug. 31, 2021

(54) EXERCISE BIOFEEDBACK USING SENSOR-EQUIPPED ATHLETIC GARMENTS

(71) Applicant: Mad Apparel, Inc., Redwood City, CA (US)

(72) Inventors: Christopher John Wiebe, Burlingame, CA (US); Dhananja Pradhan Jayalath, Redwood City, CA (US); Rose Yao, San Francisco, CA (US)

(73) Assignee: Mad Apparel, Inc., Redwood City, CA (US)

( * ) Notice: Subject to any disclaimer, the term of this patent is extended or adjusted under 35 U.S.C. 154(b) by 0 days.

(21) Appl. No.: 16/431,505

(22) Filed: Jun. 4, 2019

(65) Prior Publication Data

US 2019/0282856 A1 Sep. 19, 2019

Related U.S. Application Data

(63) Continuation of application No. 15/356,354, filed on Nov. 18, 2016, now Pat. No. 10,357,688.

(51) Int. Cl.
*A63B 24/00* (2006.01)
*A61B 5/00* (2006.01)
(Continued)

(52) U.S. Cl.
CPC .......... *A63B 24/0075* (2013.01); *A41D 1/002* (2013.01); *A61B 5/0024* (2013.01);
(Continued)

(58) Field of Classification Search
CPC ............ A63B 24/0075; A63B 24/0062; A63B 24/0006; G09B 19/003; A61B 5/0024;
(Continued)

(56) References Cited

U.S. PATENT DOCUMENTS 6,623,427 B2  9/2003 Mandigo
9,445,759 B1  9/2016 Lamego et al.
(Continued)

FOREIGN PATENT DOCUMENTS

WO   WO 91/011221 A1   8/1991
WO   WO 2016/149751 A1   9/2016

OTHER PUBLICATIONS

Tank, Patrick W., Muscles of the Lower Limb, 2009, University of Arkansas for Medical Sciences, http://anatomy.uams.edu/muscles_lowerlimb.html (Year: 2009).*

(Continued)

*Primary Examiner* — Catherine M Voorhees
(74) *Attorney, Agent, or Firm* — Fenwick & West LLP

(57) ABSTRACT

An exercise feedback system monitors the performance of athletes wearing a garment with sensors while exercising. The sensors generate physiological data such as muscle activation data, heart rate data, or data describing the athlete's movement. The system extracts features from the physiological data and compares the features with reference exercise data to determine metrics of performance and biofeedback. Based on the physiological data, the system may also modify exercise training programs for the athlete. The exercise feedback system can display the biofeedback using visuals or audio, as well as modified exercise training programs, via the athlete's client device in real time while the athlete is exercising. By reviewing the biofeedback, the athlete may correct the athlete's exercise form to properly use the target muscles for the exercise, or change the certain workouts to personalize the training program.

20 Claims, 13 Drawing Sheets

(51) Int. Cl.
*A61B 5/0245* (2006.01)
*A61B 5/22* (2006.01)
*A41D 1/00* (2018.01)
*G09B 19/00* (2006.01)
*A61B 5/389* (2021.01)
*A61B 5/11* (2006.01)
*A61B 5/318* (2021.01)

(52) U.S. Cl.
CPC ............ *A61B 5/0245* (2013.01); *A61B 5/222* (2013.01); *A61B 5/389* (2021.01); *A61B 5/486* (2013.01); *A61B 5/6804* (2013.01); *A63B 24/0006* (2013.01); *A63B 24/0062* (2013.01); *G09B 19/003* (2013.01); *G09B 19/0038* (2013.01); *A61B 5/1118* (2013.01); *A61B 5/1123* (2013.01); *A61B 5/318* (2021.01); *A61B 5/7435* (2013.01); *A61B 2503/10* (2013.01); *A63B 2024/0012* (2013.01)

(58) Field of Classification Search
CPC ..... A61B 5/0245; A61B 5/0488; A61B 5/222; A61B 5/6804; A61B 5/486; A61B 5/118; A41D 1/002
See application file for complete search history.

(56) References Cited

U.S. PATENT DOCUMENTS

| | | | |
|---|---|---|---|
| 9,720,515 B2 | 8/2017 | Wagner et al. | |
| 10,065,074 B1* | 9/2018 | Hoang | ................. G09B 19/003 |
| 10,357,688 B2* | 7/2019 | Wiebe | ................. G09B 19/0038 |
| 10,362,993 B2 | 7/2019 | Wiebe et al. | |
| 2005/0107719 A1 | 5/2005 | Arad (Abbound) | |
| 2005/0177059 A1 | 8/2005 | Koivumaa et al. | |
| 2006/0136173 A1 | 6/2006 | Case et al. | |
| 2007/0232453 A1 | 10/2007 | Hanoun | |
| 2008/0262392 A1 | 10/2008 | Ananny et al. | |
| 2009/0171233 A1 | 7/2009 | Lanfermann et al. | |
| 2010/0268477 A1 | 10/2010 | Mueller et al. | |
| 2010/0312508 A1 | 12/2010 | Mott et al. | |
| 2012/0004696 A1 | 1/2012 | Sun et al. | |
| 2012/0071732 A1 | 3/2012 | Grey et al. | |
| 2012/0143093 A1 | 6/2012 | Stirling et al. | |
| 2012/0271143 A1 | 10/2012 | Aragones et al. | |
| 2013/0041590 A1 | 2/2013 | Burich et al. | |
| 2013/0136301 A1 | 5/2013 | Abrahamsson et al. | |
| 2014/0135593 A1* | 5/2014 | Jayalth | ................. A61B 5/0004 600/301 |
| 2014/0142459 A1 | 5/2014 | Jayalth et al. | |
| 2014/0235965 A1 | 8/2014 | Tran | |
| 2014/0318699 A1 | 10/2014 | Longinotti-Buitoni et al. | |
| 2014/0378858 A1 | 12/2014 | Armitage et al. | |
| 2015/0088284 A1 | 3/2015 | Hendricks et al. | |
| 2015/0120016 A1 | 4/2015 | Houmanfar et al. | |
| 2015/0148619 A1 | 5/2015 | Berg et al. | |
| 2015/0230719 A1 | 8/2015 | Berg et al. | |
| 2015/0272482 A1 | 10/2015 | Houmanfar et al. | |
| 2015/0272483 A1* | 10/2015 | Etemad | ................. A61B 5/0488 600/409 |
| 2015/0272501 A1* | 10/2015 | Maceachern | ........ A61B 5/6824 600/301 |
| 2015/0282768 A1 | 10/2015 | Luna et al. | |
| 2015/0309563 A1 | 10/2015 | Connor | |
| 2015/0351690 A1 | 12/2015 | Toth et al. | |
| 2015/0366504 A1 | 12/2015 | Connor | |
| 2016/0038083 A1 | 2/2016 | Ding et al. | |
| 2017/0071548 A1 | 3/2017 | Wiebe et al. | |
| 2017/0173391 A1 | 6/2017 | Wiebe et al. | |
| 2018/0133551 A1 | 5/2018 | Chang et al. | |
| 2018/0140901 A1 | 5/2018 | Wiebe et al. | |
| 2018/0140902 A1 | 5/2018 | Wiebe et al. | |
| 2019/0029594 A1* | 1/2019 | Jiang | ..................... A63B 71/06 |
| 2019/0046107 A1 | 2/2019 | Jang et al. | |
| 2019/0046839 A1 | 2/2019 | Jang et al. | |
| 2019/0076699 A1 | 3/2019 | Wiebe et al. | |
| 2019/0282856 A1 | 9/2019 | Wiebe et al. | |
| 2019/0290181 A1 | 9/2019 | Mrvaljevic et al. | |
| 2019/0343459 A1 | 11/2019 | Korzinov et al. | |
| 2019/0344121 A1 | 11/2019 | Wells et al. | |

OTHER PUBLICATIONS

PCT International Search Report and Written Opinion, PCT Application No. PCT/US2016/067372, dated Apr. 12, 2017, 24 pages.

United States Office Action, U.S. Appl. No. 15/356,354, dated Oct. 26, 2018, 14 pages.

United States Office Action, U.S. Appl. No. 15/356,354, dated Jun. 6, 2018, 15 pages.

United States Office Action, U.S. Appl. No. 15/356,354, dated Feb. 14, 2018, 13 pages.

International Search Report and Written Opinion, PCT Application No. PCT/US2018/046565, dated Dec. 7, 2018, 18 pages.

* cited by examiner

| Monday | Tuesday | Wednesday | Thursday | Friday |
|---|---|---|---|---|
| Week 1 ||||||

| Strength – 3 Sets<br>Bench Press<br>   8 x 180 lbs<br>Rest<br>   1 minute   ～650 | | | | Strength – 3 Sets<br>Bench Press<br>   8 x 190 lbs<br>655～ Rest<br>   1 minute |

Week 2

| Strength – 3 Sets<br>Bench Press<br>   8 x 200 lbs<br>Rest<br>   1 minute   ～660 | | | | |

FIG. 6E

| Monday | Tuesday | Wednesday | Thursday | Friday |
|---|---|---|---|---|

Week 1

| Strength – 3 Sets<br>Bench Press<br>   8 x 180 lbs<br>Rest<br>   1 minute   ～650 | 665～ Strength – 3 Sets<br>Overhead Press<br>   5 x 85 lbs<br>Rest<br>   1 minute | | 655～ Strength – 4 Sets<br>Bench Press<br>   8 x 150 lbs<br>Rest<br>   1 minute | |

Week 2

| Strength – 4 Sets<br>Bench Press<br>   8 x 160 lbs<br>Rest<br>   1 minute   ～660 | | | | 670～ Strength – 4 Sets<br>Bench Press<br>   8 x 170 lbs<br>Rest<br>   1 minute |

Receive physiological data from a garment worn by a user while performing an exercise.
710

Compare the physiological data to reference data selected based on the exercise.
720

Generate biofeedback based on the comparison.
730

Provide the biofeedback to a client device of the user.
740

FIG. 7

EXERCISE BIOFEEDBACK USING SENSOR-EQUIPPED ATHLETIC GARMENTS

CROSS REFERENCE TO RELATED APPLICATIONS

This application is a Continuation co-pending U.S. application Ser. No. 15/356,354, filed Nov. 18, 2016, which is incorporated by reference in its entirety.

BACKGROUND

1. Field of Art

This description generally relates to sensor-equipped athletic garments, and specifically to detecting athletic performance using sensor-equipped athletic garments and providing exercise feedback in response.

2. Description of the Related Art

Sensors record a variety of information about the human body. For example, electrocardiograph (ECG) electrodes can measure electrical signals from the skin of a person that are used to determine the person's heart rate. In addition, electromyography (EMG) electrodes can measure electrical activity generated by a person's muscles. Heart rate and muscle movement information may be useful for evaluating the person's physiological condition, for instance, while exercising. This information may also be used to evaluate the performance of an athlete during strength and conditioning training.

When exercising, athletes and coaches may not be able to determine whether the athlete is properly performing certain types of exercises. For example, a bench press exercise has a proper form that requires an athlete to focus on exerting a particular set of muscles in the upper body. Performing exercises with improper form results in suboptimal exercise training for athletes, and may even cause injury to an athlete. Also, without proper form, the athlete may not be gaining the intended benefit from an exercise (e.g., strengthening a specific muscle group targeted by the exercise). Additionally, athletes may not recognize when they reach a level of fatigue that is negatively impacting their exercise performance. Currently, an athlete can work with a coach who observes the athlete's performance and provides feedback. However, it may not be practical for an athlete to exercise with a coach at all times. Further, feedback provided by coaches can be subjective, based on how the athlete feels at a given time, or a rough observation by the human eye of the motion of the athlete.

SUMMARY

An exercise feedback system monitors the exercise performance of athletes. Athletes wear a garment with sensors while exercising. The sensors generate physiological data such as muscle activation data, heart rate data, or data describing the athlete's movement. The exercise feedback system extracts features from the physiological data and compares the features with reference exercise data to determine metrics of performance. For example, the reference exercise data indicates the athlete should primarily use the pectorals and triceps muscles while performing bench press exercises. If features based on the muscle activation data indicate that an athlete is correctly using the primary muscles, the exercise feedback system determines a satisfactory metric of performance. Otherwise, the exercise feedback system determines an unsatisfactory metric of performance and informs the athlete via biofeedback. For example, the exercise feedback system displays the biofeedback using visuals or audio via the athlete's mobile device in real time while the athlete is exercising. By reviewing the biofeedback, the athlete may correct the athlete's exercise form to properly use the primary muscles for the exercise. Incorporating physiological data, muscle usage data, exertion data, timing data, and/or fatigue data into the process of providing exercise feedback personalizes the athlete's training to improve training results.

BRIEF DESCRIPTION OF DRAWINGS

FIG. 6E is a user interface showing an exercise training program according to one embodiment.

FIG. 6F is a user interface showing a modified version of the exercise training program shown in FIG. 6E according to one embodiment.

FIG. 7 is a flowchart of a process for providing exercise feedback according to one embodiment.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

I. System Overview

Figure 1:
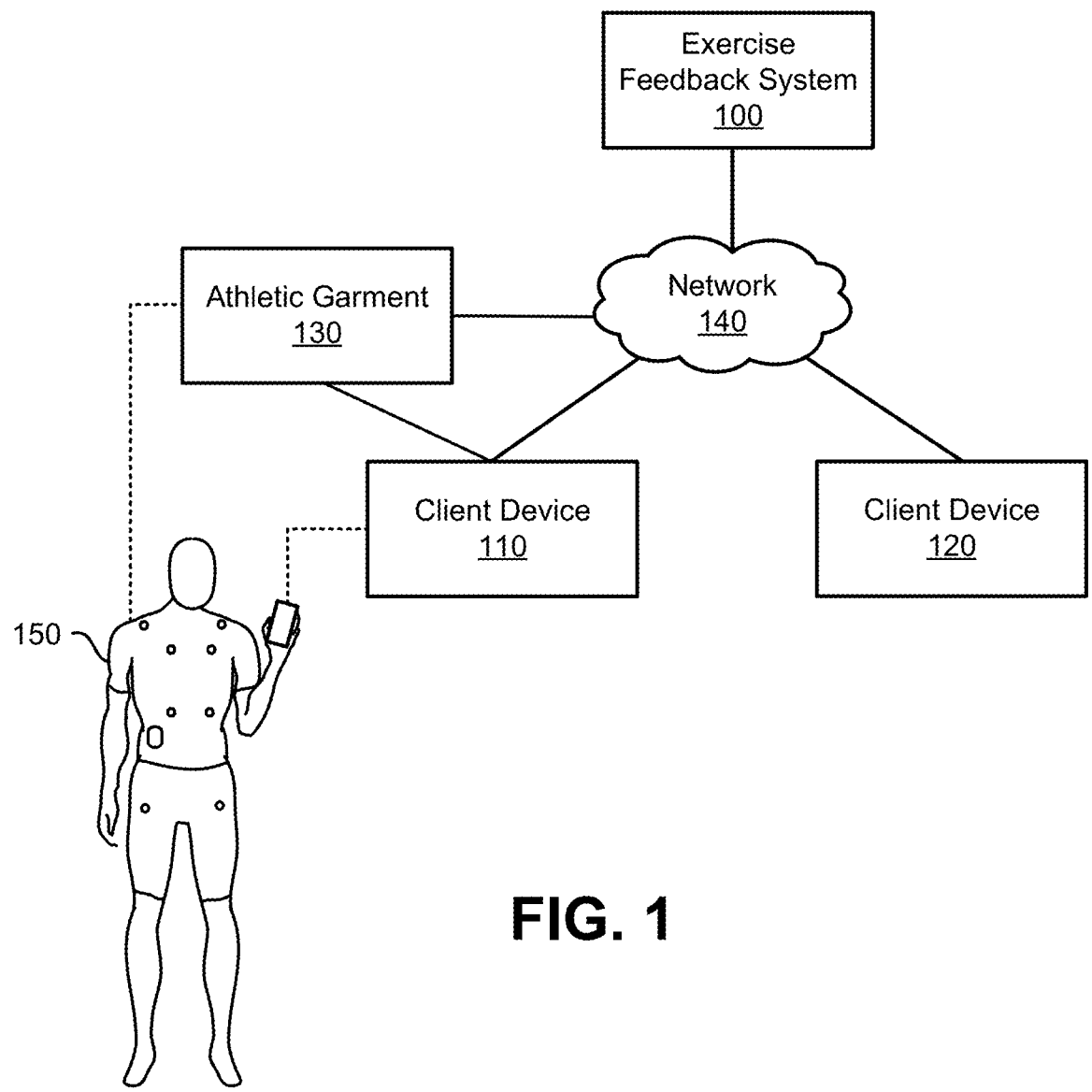
FIG. 1 is a diagram of a system environment for monitoring exercise data according to one embodiment.

FIG. 1 is a diagram of a system environment for monitoring exercise data according to one embodiment. The system architecture includes an exercise feedback system 100, client device 110 (also referred to as an "athlete's device"), client device 120 (also referred to as a "coach's device"), and athletic garment 130 communicatively coupled together via a network 140. Users of the exercise feedback system 100 are also referred to herein as "athletes." In other embodiments, different and/or additional entities can be included in the system architecture.

The client devices 110 and 120 are computing devices capable of receiving user input as well as transmitting and/or receiving data via the network 140. A client device is a device having computer functionality, such as a smartphone, personal digital assistant (PDA), a mobile telephone, tablet, laptop computer, desktop computer, or another suitable device. In one embodiment, a client device executes an application allowing a user of the client device to interact with the exercise feedback system 100. For example, a client device executes a browser application to enable interaction between the client device and the exercise feedback system 100 via the network 140. In another embodiment, a client device interacts with the exercise feedback system 100 through an application programming interface (API) running on a native operating system of the client device, such as IOS® or ANDROID™.

The network 140 includes any combination of local area and/or wide area networks, including both wired and/or wireless communication systems. In one embodiment, the network 140 uses standard communications technologies and/or protocols. For example, the network 140 includes communication links using technologies such as Ethernet, 802.11, worldwide interoperability for microwave access (WiMAX), 3G, 4G, code division multiple access (CDMA), digital subscriber line (DSL), BLUETOOTH®, Wi-Fi, ZIG-BEE®, other suitable close-range networks, etc. Examples of networking protocols used for communicating via the network 140 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network 140 may be represented using any suitable format, such as hypertext markup language (HTML) or extensible markup language (XML). In some embodiments, all or some of the communication links of the network 140 may be encrypted using any suitable technique or techniques.

An athlete 150 wears the athletic garment 130 while performing exercises. The athletic garment 130 records physiological data, e.g., muscle activation data, heart rate data, or motion data, of the athlete. Based on the physiological data, the exercise feedback system 100 generates exercise feedback personalized for the athlete. Further, a coach of the athlete can view the exercise feedback on the coach's device 120 and provide additional feedback for the athlete. The athlete can view the exercise feedback and any additional feedback displayed on a user interface of the athlete's device 110.

II. Athletic Garment

Figure 2:
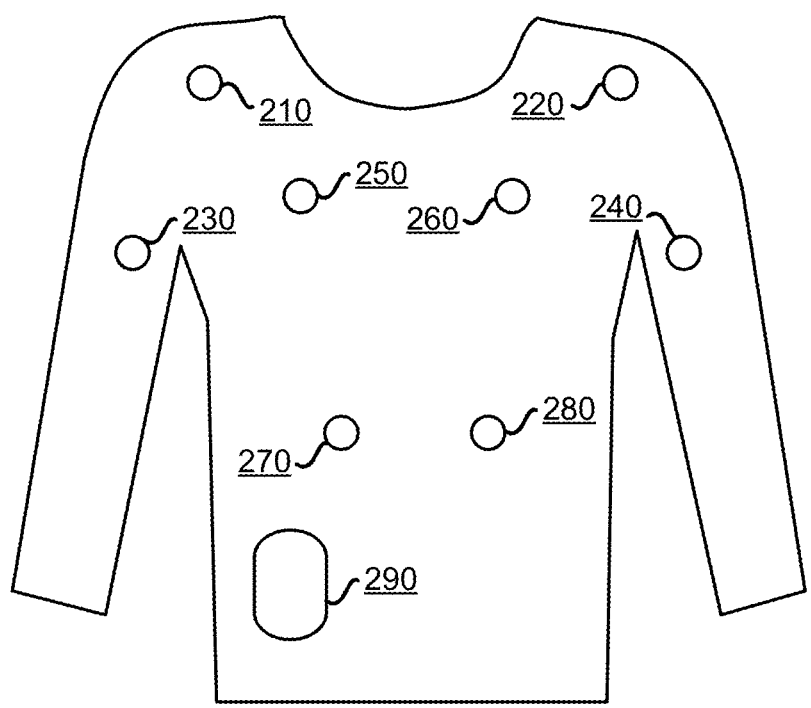
FIG. 2 is a diagram of a sensor-equipped athletic garment according to one embodiment.

FIG. 2 is a diagram of a sensor-equipped athletic garment 130 according to one embodiment. The athletic garment 130 includes sensors that contact the skin of an athlete wearing the athletic garment 130. For example, the sensors can be electrodes that measure electromyography (EMG) signals (electrical signals caused by muscle cells) also referred to as muscle activation data or electrocardiograph (ECG) signals (electrical signals caused by depolarization of the user's heart muscle in particular) also referred to as heart rate data. The sensors may also include other types of sensors such as accelerometers and gyroscopes (which generate motion data based on the athlete's movement), temperature sensors, pressure sensors, humidity sensors, etc. The sensors generate physiological data of the athlete based on the measured signals. The sensors are communicatively coupled to a processing unit 290. The processing unit 290 can aggregate and analyze the physiological data from the sensors. The processing unit 290 can also provide the physiological data to the athlete's device 110, coach's device 120, or exercise feedback system 100 via the network 140.

In the embodiment shown in FIG. 2, the athletic garment 130 includes eight sensors that record muscle activation data from the athlete's muscles nearby each sensor. In particular, sensors 210 and 220 located on the right and left shoulder of the athletic garment 130 can record muscle activation data of the athlete's deltoid muscles. Sensors 230 and 240 located on the right and left sleeves of the athletic garment 130 can record muscle activation data of the athlete's triceps and/or bicep muscles. Sensors 250 and 260 located on the right and left chest of the athletic garment 130 can record muscle activation data of the athlete's pectoral muscles. Sensors 270 and 280 located on the right and left abdomen of the athletic garment 130 can record muscle activation data of the athlete's abdominal and oblique muscles. Though the athletic garment 130 shown in FIG. 2 includes eight sensors and the processing unit 290, in other embodiments, the athletic garment 130 can include any number of sensors or other types of components or electronics at any location or configuration within the athletic garment 130.

It should be noted that while the athletic garment 130 shown in FIG. 2 is a long sleeve shirt, the principles described herein apply equally to any garment, including but not limited to a short sleeved shirt, a tank top, pants, shorts, or any other suitable garment. In embodiments where the athletic garment 130 is a pant, sensors of the athletic garment 130 can record muscle activation data from muscles on an athlete's lower body, e.g., quadriceps (also referred to herein as "quad" or "quads"), gluteus maximus (also referred to herein as "glute" or "glutes"), hamstrings, calves, and the like.

III. Exercise Plan Model

Figure 3:
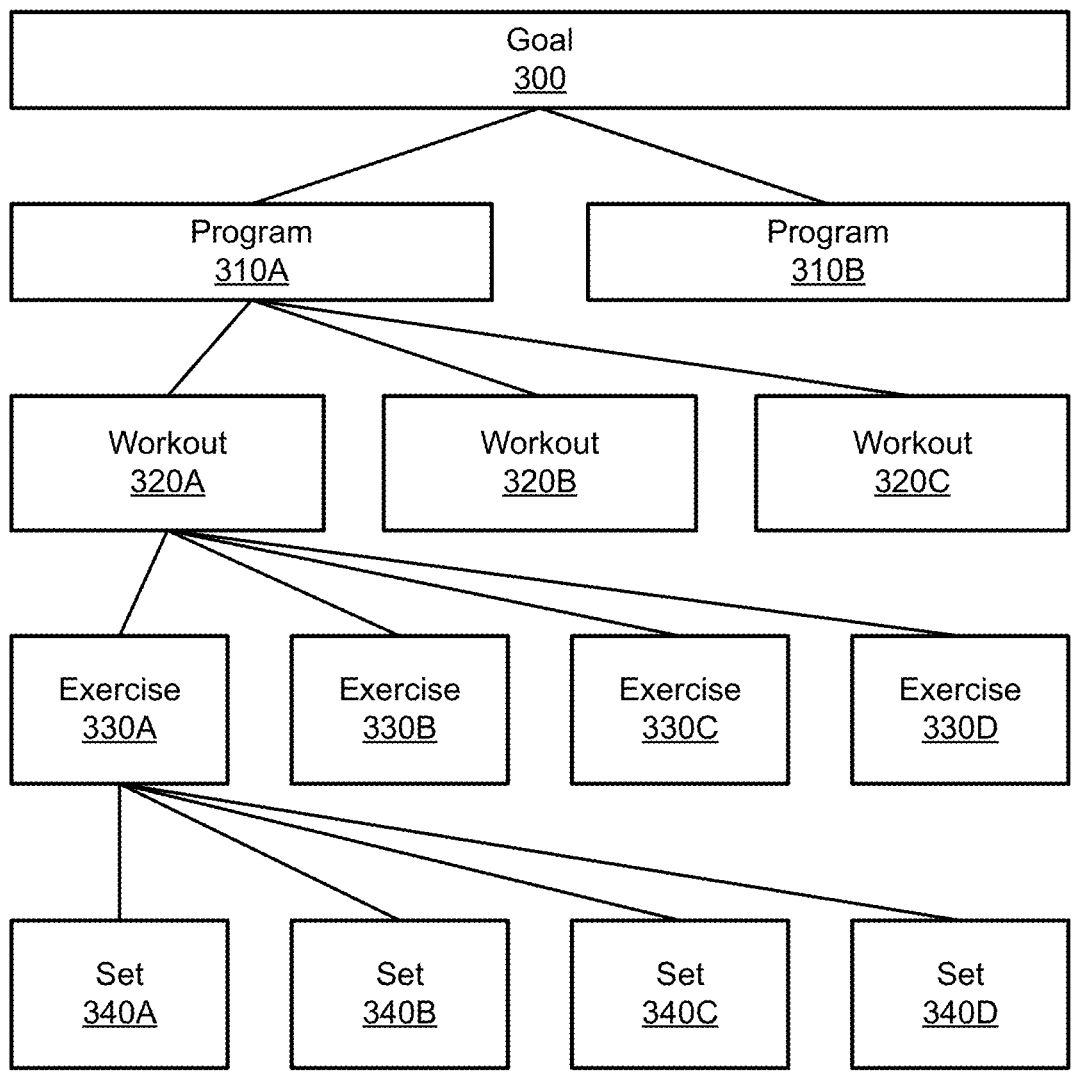
FIG. 3 is a diagram of an exercise plan model used by the exercise feedback system according to one embodiment.

FIG. 3 is a diagram of an exercise plan model used by the exercise feedback system 100 according to one embodiment. The exercise plan model is a hierarchal model with a goal, programs, workouts, exercises, and sets. The goal 300 is an objective that an athlete wants to work towards or achieve. The goal can describe a general athletic characteristic, e.g., power, strength, hypertrophy, endurance, speed, or flexibility. Additionally, the goal can describe more specific athletic characteristics, e.g., vertical leap height, a long distance running metric, or arm dexterity. Goals can describe a training objective for a particular sport, e.g., football or basketball, or player position for a sport, e.g., lineman for football or point guard for basketball. Further, goals can describe other objectives that the athlete is pursuing, e.g., losing weight, gaining muscle mass, or toning arm muscles.

A goal is associated with one or more programs. An athlete can complete programs, also referred to as exercise training programs, to help achieve the corresponding goal. In the embodiment shown in FIG. 3, the goal 300 is associated with the programs 310A and 310B. In one example where the goal is strength, the programs can include "upper body strength," "lower body strength," and "core body strength." In another example where an athlete's goal is to train to play as a football lineman, the programs can include "lateral movement," "explosive power," and "upper body strength," e.g., because these programs focus on athletic skills that are useful for football linemen. In yet another example where an athlete's goal is to train to play as a basketball point guard, the programs can include "lateral movement," "basketball dribbling," and "arm strength," e.g., because these programs focus on athletic skills that are useful for basketball point guards. Thus, the programs are customized for an athlete based on the athlete's specific goals.

Each program is associated with one or more workouts. Workouts are sets of exercises that an athlete can complete consecutively or in one activity session as part of the corresponding program. In the embodiment shown in FIG. 3, the program 310A is associated with the workouts 320A, 320B, and 320C. In one example where the program is "upper body strength," the workouts can include "shoulder strength," "upper back strength," and "chest strength," e.g., because these workouts each help develop strength in upper body muscles. In another example where the program is "lateral movement," the workouts can include "lateral speed," "lateral agility," and "lateral explosiveness," e.g., because these workouts each help develop different lateral movement skills.

Each workout is associated with one or more exercises. An athlete can complete exercises as part of the corresponding workout. In the embodiment shown in FIG. 3, the workout 320A is associated with the exercises 330A, 330B, 330C, and 330D. In one example where the workout is "upper body strength," the exercises can include "bench press" and "overhead squat". In another example where the workout is "lateral speed," the exercises can include "lateral lunge" and "lateral shuffle."

Each exercise is associated with one or more sets. An athlete can complete sets as part of the corresponding exercise. In the embodiment shown in FIG. 3, the exercise 330A is associated with the sets 340A, 340B, 340C, and 340D. Depending on the type of a set, the set is associated with at least one of a weight, a number of repetitions, a distance, or a duration in time for an athlete to perform the exercise. In one example where the exercise is "bench press," the set indicates that the athlete should perform eight repetitions lifting 180 pounds per repetition. In another example where the exercise is "lateral shuffle," the set indicates that the athlete should perform a lateral shuffle for 5 meters in both the left and right directions for 5 repetitions, or perform a lateral shuffle back and forth for 3 consecutive minutes.

IV. Exercise Feedback System

Figure 4A:
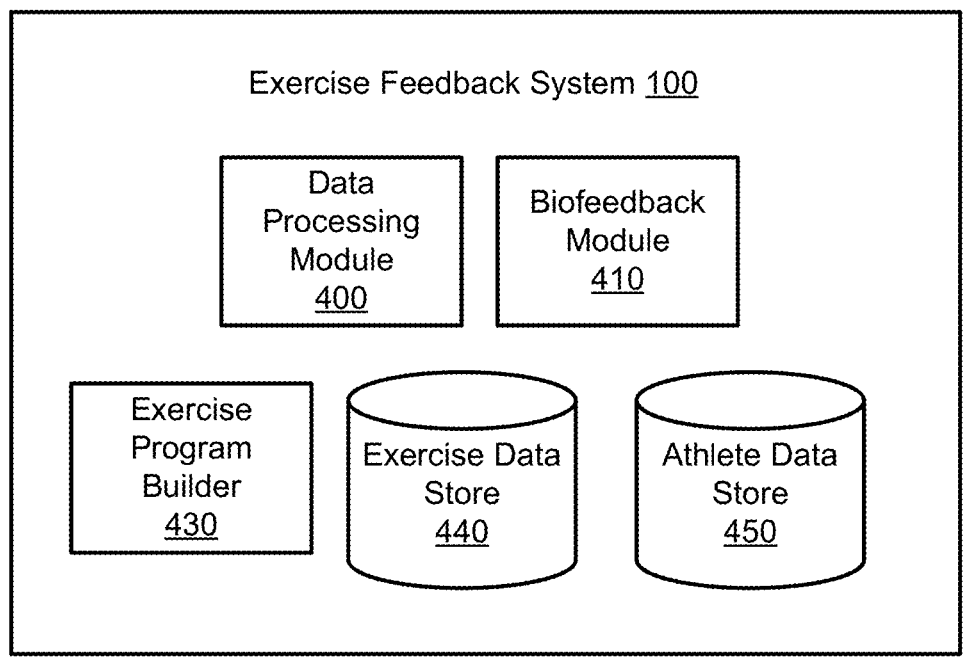
FIG. 4A is a block diagram of an exercise feedback system according to one embodiment.

FIG. 4A is a block diagram of the exercise feedback system 100 according to one embodiment. The exercise feedback system 100 includes a data processing module 400, biofeedback module 410, exercise program builder 430, exercise data store 440, and athlete data store 450. In other embodiments, the exercise feedback system 100 may include additional, fewer, or different components for various applications, which are not shown so as to not obscure the details of the system architecture.

The data processing module 400 processes physiological data generated by sensors of an athletic garment (e.g., athletic garment 130 shown in FIG. 2). The exercise feedback system can receive the physiological data from the athlete's device 110 or the processing unit 290 of the athletic garment 130. The data processing module 400 can process the physiological data by performing noise filtering or feature extraction. Features can include a heart rate or level of muscle activation for a certain muscle of an athlete. For example, the data processing module 400 determines the heart rate, e.g., in beats per minute, of an athlete based on parameters from electrocardiograph data. In another example, the data processing module 400 calculates the amount of time that the heart rate of the athlete was within a predetermined percentage range of the athlete's maximum heart rate. In another example, the data processing module 400 determines a level of muscle activation for a particular muscle of an athlete based on the muscle activation data, e.g., an average of the muscle activation data or a peak amplitude of the muscle activation data. The level of muscle activation can be represented as "low," "medium," or "high," a percentage value, or another other suitable range of values.

In one embodiment, the data processing module 400 extracts features that represent the comparative contribution of different muscle groups to an exercise. The activation of a muscle over time can be accumulated to represent the energy or work expended by the muscle during the movement (e.g., of the exercise). The data processing module 400 may calculate the percentage contribution of the muscle to the movement based on the ratio of work calculated for a given muscle to the sum of work calculated for all muscles measured.

Further, the data processing module 400 can extract temporal patterns from the physiological data. For example, the data processing module 400 determines the time difference between a first muscle activation and a second muscle activation, which may indicate how closely an athlete is performing an exercise with proper form and whether the athlete is using the correct sequence of muscles. The data processing module 400 may determine sequencing and form of an athlete's performance of an exercise by comparing the time difference between different events of muscle activation data such as the start, end, or peak amplitude for each muscle. Additionally, the data processing module 400 determines timestamps of an athlete's movements based on motion data, e.g., a timestamp corresponding to when the athlete started an exercise, ended an exercise, or performed a certain athletic movement such as a jump, sprint, lift of an arm, or specific phases of a movement such as the lowering or raising phase of a squat. The data processing module 400 can store the extracted features in the athlete data store 450 along with information identifying the corresponding athlete.

The data processing module 400 can determine features based on a computation of one or more other features of physiological data. For example, the data processing module 400 computes a ratio of a first level of muscle activation (of an athlete's left biceps muscle) to a second level of muscle activation (of an athlete's right biceps muscle), which can indicate the athlete's balance, form, or other types of metrics.

As another example, the data processing module 400 computes a level of aerobic fatigue or endurance based on an athlete's heart rate and/or the duration of time spent within different percentage ranges of the athlete's maximum heart rate. Additionally, the data processing module 400 may determine a level of anaerobic fatigue or endurance based on an accumulation of muscle activation over a predetermined period of time, e.g., representing a rep, set, workout, or program. The accumulation of muscle activation over time represents the energy or work expended by the muscle and may be aggregated across all muscle groups measured to calculate an overall total work or load placed on the athlete's body. The data processing module 400 may use this information to predict athlete fatigue.

The biofeedback module 410 generates biofeedback for users of the exercise feedback system 100 based on features extracted by the data processing module 400. The biofeedback indicates a metric of performance (e.g., satisfactory or unsatisfactory) of an athlete performing exercises. The biofeedback module 410 can store the biofeedback in the athlete data store 450 along with information identifying the corresponding athlete. The biofeedback module 410 can compare the extracted features with features based on reference exercise data from the exercise data store 440. In one example, the reference exercise data indicates a target range of heart rate (e.g., heart rate after exercising or heart rate while performing high intensity exercises) based on demographic information of an athlete (e.g., age or gender). If the athlete's heart rate indicated by the extracted features falls within the corresponding target range, then the biofeedback module 410 generates biofeedback indicating that the athlete has a satisfactory heart rate.

In another example, the reference exercise data indicates target muscle activation levels based on a given type of exercise. For instance, for a squat exercise, the reference exercise data indicates that the quadriceps or glutes should fall within a given range of muscle activation. Additionally, for a bench press exercise, the reference exercise data indicates that the pectorals and deltoids should have a high level of muscle activation and that the triceps should have a medium to high level of muscle activation. The biofeedback module 410 can compare the athlete's actual muscle activation to the target muscle activation information. If the extracted features indicate that an athlete's muscle activation levels do not meet the target muscle activation levels, biofeedback module 410 generates biofeedback indicating that the athlete performed the exercise with an unsatisfactory effort. If the extracted features indicate that an athlete's muscle activation levels are not balanced between corresponding muscles (e.g., quadriceps in the left leg and quadriceps in the right leg), biofeedback module 410 generates biofeedback indicating that the athlete has unsatisfactory balance. Further, the biofeedback can indicate that the athlete is activating the incorrect muscles for a particular exercise, e.g., the deltoids are activated more than the pectorals or triceps during a bench press exercise.

In yet another example, the reference exercise data indicates baseline motion profiles for various types of exercises. The baseline motion profiles are based on motion data generated by sensors (e.g., accelerometers or gyroscopes) worn by a reference athlete, e.g., an expert that previously performed a given exercise. The baseline motion profiles can include a first profile generated when the reference athlete performed the given exercise using proper form and second profile generated when the reference athlete performed the given exercise using an improper form. The biofeedback module 410 can compare the athlete's actual motion profiles to the baseline motion profiles. If the extracted features match features of the first profile, the biofeedback module 410 generates biofeedback indicating that the athlete is performing the exercise using proper form. If the extracted features match features of the second profile, the biofeedback module 410 generates biofeedback indicating aspects of the athlete's form that deviate from desired proper form (e.g., for a squat exercise, the athlete is not keeping their shins straight, sitting back, and pushing through their heels when raising out of the squat position). In addition to baseline motion profiles, the reference exercise data can also include baseline muscle activation data, timing data, fatigue data, or heart rate data of an expert while performing a particular exercise. The biofeedback module 410 can use any of the baseline data for comparison with the features extracted from the user's performance of an exercise.

In one embodiment, by leveraging muscle activation, timing, fatigue, or heart rate data across populations of different athletic skill, the exercise feedback system 100 determines targets associated with muscle activation, timing, fatigue, or heart rate metrics to provide an understanding to the athlete regarding how a given metric should change to demonstrate progression. For example, based on data of a population of athletes that have well trained lower body posterior chains and proficiency in completing a deadlift movement, the exercise feedback system 100 determines that the target (e.g., average) percentage contribution of the glute and hamstring muscles (e.g., based on the work metric) to the deadlift movement are approximately 40% and 30%, respectively. In an example use case, a given athlete is loading more of their quadriceps muscles, resulting in lower glute and hamstring contributions, e.g., 25% and 20%, respectively. The exercise feedback system 100 provides the given athlete with feedback to show their muscle contribution during the deadlift movement set-by-set to track progress towards the target percentage contributions.

The biofeedback module 410 can generate biofeedback indicating a level of fatigue of the athlete. For example, the athlete performs the first bench press exercise of a set using proper form and performs the fifth bench press exercise of the set (e.g., a set of eight total exercises) using improper form. As the athlete fatigues, the athlete's quality of movement may suffer and the athlete deviates from the proper form. Using the bench press exercise as an example, as the athlete fatigues, if the athlete's chest and triceps muscle are weak, the athlete's deltoids may compensate and thus have a much greater contribution during the fifth set as compared to the first set. The biofeedback module 410 may alert the athlete about this change and provide biofeedback to correct the athlete's form. Further, the biofeedback module 410 may provide an alert to a client device of the athlete's coach. The biofeedback module 410 can also determine the level of fatigue based on heart rate data and muscle activation data.

The biofeedback module 410 can generate biofeedback indicating that the athlete violated one or more exercise rules while performing an exercise. The biofeedback module 410 retrieves exercise rules from the exercise data store 440. For example, an exercise rule indicates that the athlete should use the pectorals as the primary source of strength and the triceps as a secondary source of strength when performing bench press exercises. Exercise rules may be categorized based on a level of priority. For example, an exercise rule indicating that an athlete is using improper form (e.g., exerting quad muscles too much when performing a deadlift exercise) is high priority, e.g., because failing to correct improper form could injure the athlete. In contrast, an exercise rule indicating that the user is slightly unbalanced when performing an exercise may have a lower priority. In some embodiments, the biofeedback module 410 generates biofeedback based on higher priority exercise rules before generating biofeedback based on lower priority exercise rules.

The biofeedback module 410 can generate biofeedback for an athlete based on the athlete's previously saved biofeedback in the athlete data store 450 and based on performance trends determined from the saved biofeedback. Thus, the biofeedback module 410 can compare the athlete's current performance to past performances and determine performance trends over a period of time (e.g., a week, month, or year). For example, the performance trends indicate that the athlete's form for a squat exercise is gradually becoming more similar to the target proper form based on reference exercise data. As another example, the performance trends indicate that the athlete is achieving satisfactory metrics of performance for bench press exercises while increasing the amount of weight lifted per exercise by an average of five pounds per month for the last six months. The biofeedback module 410 may compare performance trends between sets within a given workout for a given exercise, or across multiple workouts. The biofeedback module 410 may also compare overall workout level data, e.g., accumulated muscle activation data over the workout. Based on the work metric, the biofeedback module 410 can compare loading on different muscles between workouts and evaluate if certain muscle groups are being over-trained or under-trained with respect to other muscle groups.

The biofeedback module 410 can generate biofeedback for an athlete based on information from a population of athletes of the exercise feedback system 100, e.g., stored in the athlete data store 450. The biofeedback module 410 can compare the athlete's performance with comparable other athletes categorized by demographic data, geographic data, athletic skill level (e.g., amateur or professional), or other types of athlete data, e.g., one or more given sports played by athletes, or position played by the athlete in the sport. For example, the biofeedback module 410 generates biofeedback indicating that the athlete is lifting ten pounds more than the average weight lifted by other athletes who are also males and in the same weight group, e.g., 150 to 180 pounds. In another example, the biofeedback indicates that the athlete's heart rate while performing a given cardio exercise is 10% lower on average than those other athletes while performing the given cardio exercise who are in a same age range, e.g., 20 to 30 years old. In another example, the biofeedback module 410 compares the athlete's performance to more proficient or advanced athletes to understand the difference and target for a given metric, e.g. decrease the contribution of the quads by 10% and increase the contribution of the glutes by 10%.

In one embodiment, the biofeedback module 410 generates a set score indicating a metric of performance of a set of exercises performed by an athlete. The biofeedback module 410 may generate the set score based on aggregate data of muscle effort, balance, and form. A high set score can indicate that the athlete is consistently achieving or exceeding satisfactory metrics of performance for the set of exercises, e.g., by performing exercises with proper form and muscle activation. On the other hand, a low set score can indicate that the athlete has unsatisfactory metrics of performance throughout exercises in the set, e.g., by performing exercises with improper form and unbalanced muscle activation. In one embodiment, the set score is a numerical value between zero and ten. A high set score would be in the range of seven to ten, a low set score would be in the range of zero to three, and a medium (or neutral) set score would be in the range of three to seven. In other embodiments, the set score can be represented in other forms, e.g., a percentage value, a value between 0 and 100, or a letter grade such as "A," "B," "C," "D," or "F."

In one embodiment, the biofeedback module 410 generates set scores based on target metrics associated with a given exercise, e.g., whether data values indicating the athlete's exertion level, balance, and form are within a target range of values associated with the given exercise. The exertion level may be proportional to the athlete's muscle activation during the given exercise. The balance for a particular muscle group is based on whether the left and right muscles of the group have approximately the same muscle activation or exertion levels. The form is based on whether the athlete is exerting the target muscles, and in a target sequence, for the given exercise.

The exercise program builder 430 generates exercise training programs (e.g., corresponding to a program shown in FIG. 3) for athletes of the exercise feedback system 100. The exercise program builder 430 can generate an exercise training program based on a certain goal provided by an athlete, or can generate a set of predetermined exercise training programs that athletes can choose from. The exercise training program can include one or more workouts per day, scheduled over a duration of time, e.g., a week, month, year, etc.

The exercise program builder 430 can modify exercise training programs over time based on biofeedback from the biofeedback module 410, input information from an athlete received via the athlete's device 110, or input information from a coach of the athlete received via the coach's device 120. For example, the input information indicates that the athlete wants a more challenging exercise training program, so the exercise program builder 430 modifies exercise training programs to include more workouts, more sets of exercises, or exercises with greater amounts of weights. In another example, the input information indicates that the coach wants to reduce the number of workouts per week for an athlete because the coach views biofeedback indicating that the athlete is frequently becoming too fatigued during workouts. Thus, the program builder 430 modifies exercise training programs to include fewer workouts, fewer sets per workout, or exercises with smaller amounts of weights.

Figure 4B:
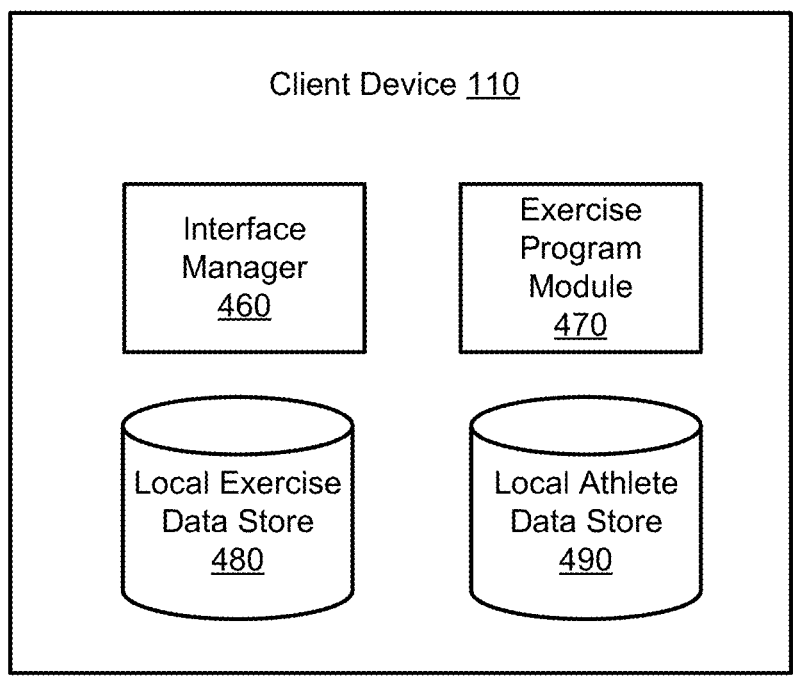
FIG. 4B is a block diagram of a client device according to one embodiment.

FIG. 4B is a block diagram of the client device 110 according to one embodiment. The client device 110 includes an interface manager 460, exercise program module 470, local exercise data store 480, and local athlete data store 490. In other embodiments, the client device 110 may include additional, fewer, or different components for various applications, which are not shown so as to not obscure the details of the system architecture. The client device 120 is substantially the same as the client device 110, though as previously noted, the client device 120 is used by a coach of the athlete using the client device 110.

In some embodiments, some or all of the functionality of the exercise feedback system 100 may be performed by or implemented within the client device 110. For example, the client device may include a biofeedback module to generate biofeedback based on physiological data received from the athletic garment 130. This can be advantageous because the client device 110 may not always have a network connection while an athlete is exercising (e.g., the athlete's gym does not have internet available). Thus, the biofeedback is generated locally on the client device 110 without having to upload the physiological data to the exercise feedback system 100 for processing.

The interface manager 460 receives physiological data from the athletic garment 130 and can provide the physiological data to the exercise feedback system 100 for further processing. The interface manager 460 receives biofeedback, set scores, exercise training programs, and other information from the exercise feedback system 100, e.g., reference exercise data or extracted features from the data processing module 400. Based on the received information, the interface manager 460 generates graphical user interfaces (further described in Sections V, VI, and VIII with reference to FIGS. 5A-F, FIGS. 6A-F, and FIGS. 9A-D) depicting the biofeedback, set scores, or exercise training programs. The interface manager 460 can store physiological data, biofeedback, set scores, or exercise training programs in the local athlete data store 490. The interface manager 460 stores the reference exercise data and extracted features in the local exercise data store 480.

The interface manager 460 can receive athlete information input by the athlete via the client device 110. The interface manager 460 can store the athlete information in the local athlete data store 490 or provide the athlete information to the exercise feedback system 100 to be stored in the athlete data store 450. The athlete information can describe, e.g., a goal of the athlete, demographic data (age or gender), geographical location, one or more sports that the athlete plays, history of injuries of the athlete, other types of data such as biometrics including weight and height. Additionally, the interface manager 460 can receive information input by a coach of the athlete via the client device 120, and provide the input information to the exercise feedback system 100.

The exercise program module 470 can modify exercise training programs received from the exercise feedback system 100. Similar to the exercise program builder 430, the exercise program module 470 modifies the exercise training programs based on physiological data, biofeedback, set scores, or input from athletes or coaches. However, the exercise program module 470 modifies the exercise training programs locally on the athlete's device 110 or coach's device 120. The exercise program module 470 can provide the modified exercise training programs to the exercise feedback system 100. In one example use case, the athlete provides input to modify an exercise training program. The exercise program module 470 modifies the exercise training program locally, but does not immediately provide the modifications to the exercise feedback system 100 because the athlete's device 110 does not have a network connection. The exercise program module 470 stores the modifications in the local athlete data store 490 and provides the modifications to the exercise feedback system 100 at a later time when the athlete's device 110 has a network connection. Afterwards, the exercise feedback system 100 can also provide the modified exercise training program to a coach's device 120 for display to the athlete's coach.

V. Example Use Case: Squat

Figure 5A:
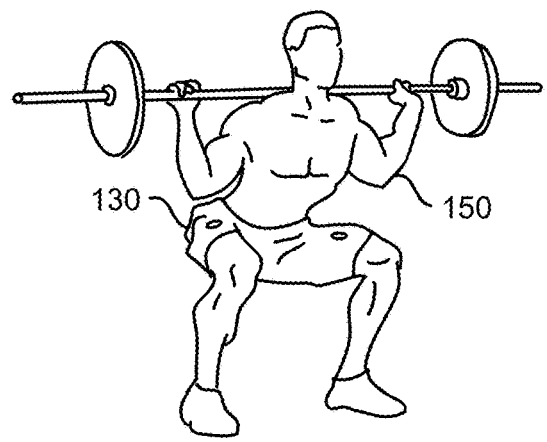
FIG. 5A is a diagram of an athlete performing a squat exercise while wearing a sensor-equipped garment according to one embodiment.
Figure 5B:
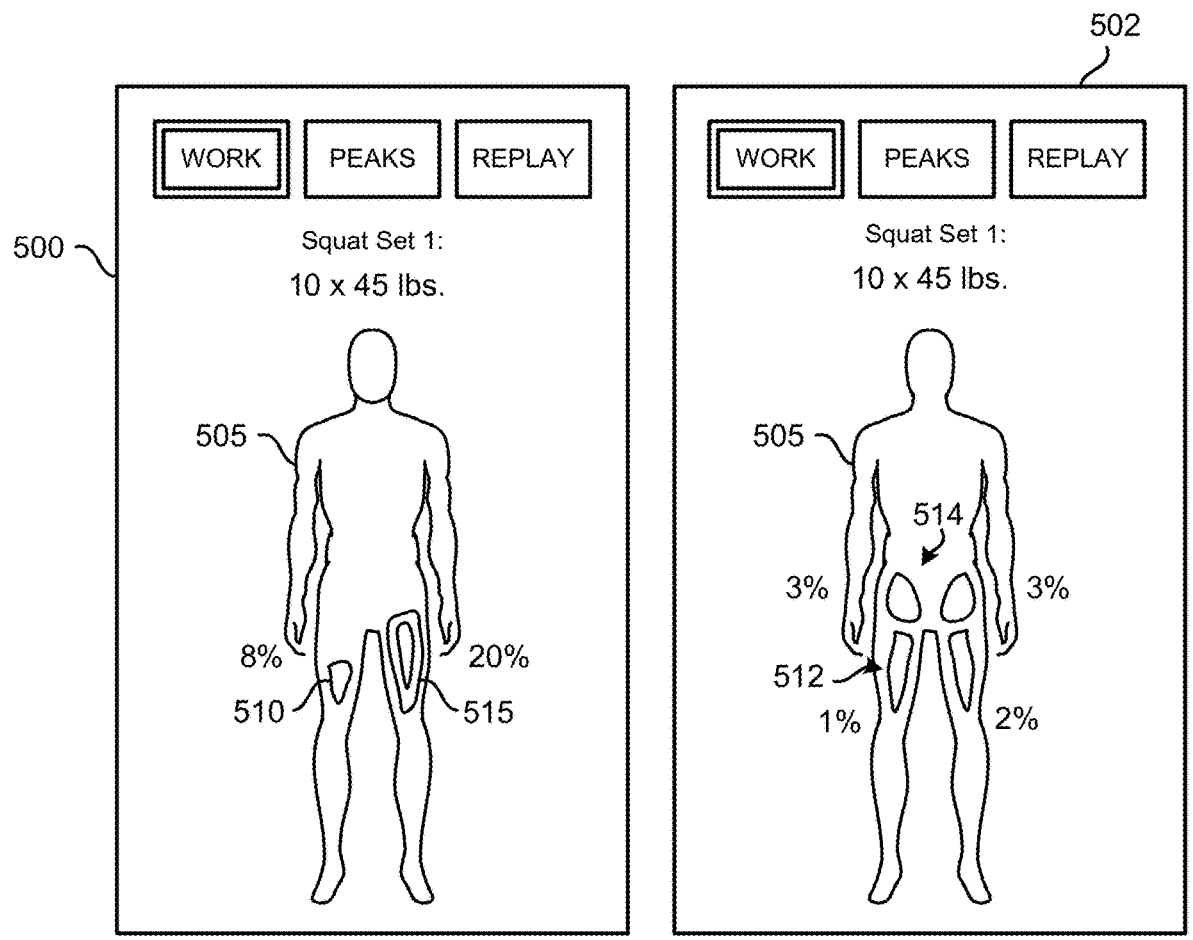
FIG. 5B is a user interface showing muscle activation feedback according to one embodiment.
Figure 5C:
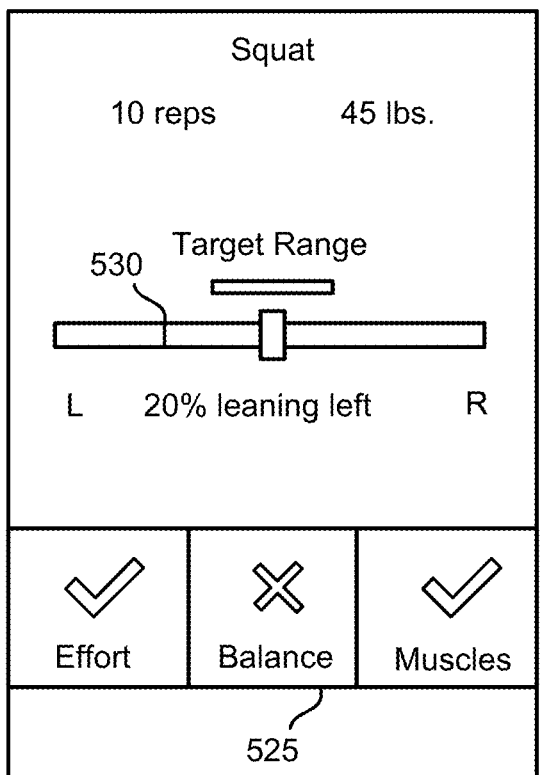
FIG. 5C is a user interface showing exercise balance feedback according to one embodiment.
Figure 5D:
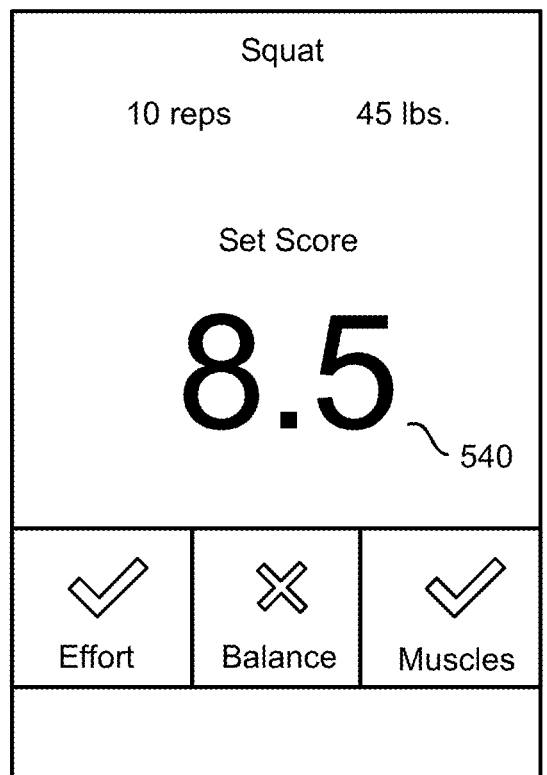
FIG. 5D is a user interface showing exercise set score feedback according to one embodiment.

FIG. 5A is a diagram of an athlete 150 performing a squat exercise while wearing a sensor-equipped garment 130 according to one embodiment. The athlete 150 is wearing the sensor-equipped athletic garment 130 (a pair of shorts) including sensors that generate muscle activation data about the athlete's lower body muscles, e.g., quadriceps and glutes. The athlete 150 may be performing a set of the squat exercise with a barbell, e.g., a set of ten repetitions with 45 pounds of weight on the barbell per repetition. FIGS. 5B-D show user interfaces generated by the interface manager 460 in real time while the athlete 150 performs the squat exercise.

FIG. 5B is a user interface 500 showing muscle activation feedback according to one embodiment. The muscle activation feedback is represented by a depiction of muscles overlaid on an image 505 of the athlete 150, e.g., based on biofeedback generated by the biofeedback module 410. In particular, the image 505 shows a metric for the athlete's right quadriceps 510 and left quadriceps 515. The metrics shown in FIG. 5B are depictions of the levels of exertion of each of the two muscles. The level of exertion may be represented as an activation intensity, contribution based on work, or any other metric output by the data processing module 400. For example, the depiction of the right quadriceps 510 is smaller than that of the left quadriceps 515 because the athlete is exerting with higher activation intensity on the left quadriceps 515. The user interface 500 may include percentages alongside the different muscles to indicate activation intensity or contribution of the corresponding muscle to the movement. For example, the percentages of 8% and 20% correspond to the right quadriceps 510 and left quadriceps 515, respectively. In addition, the depiction of level of exertion on image 505 may be shown in near real-time while the athlete is performing the exercise or may be presented as a set or workout summary after completing the exercise. FIG. 5B also shows another user interface 502 showing muscle activation feedback including a depiction of muscles on the backside of the athlete, which is also overlaid on an image 505 of the athlete 150. For example, the user interface 502 shows activation intensity of the athlete's hamstrings 512 and glutes 514, which are also activated with the quads 510 and 515 while the athlete performs a squat exercise.

FIG. 5C is a user interface 520 showing exercise balance feedback according to one embodiment. The user interface 520 shows a depiction, e.g., based on biofeedback generated by the biofeedback module 410, of three categories 525 of exercise feedback: effort, balance, and muscles. The categories 525 shown in FIG. 5C indicate that the athlete 150 is has a satisfactory metric (e.g., as indicated by the checkmark) for effort and muscles, but not for balance (e.g., as indicated by the X mark). Balance has an unsatisfactory metric, e.g., because the athlete 150 leans too far to the left when performing squat exercises. Further, the graph 530 indicates that the athlete 150 is "20% leaning left," for example, the athlete 150 is exerting approximately 20% more energy using the left quadriceps than using the right quadriceps, which is outside of a target range for balance (e.g., no more than 10% based on an exercise rule in the exercise data store 440). In other embodiments, the metric for balance may be based on other types of data such as the athlete's acceleration of each leg when jumping and landing while performing the squats, or the timing between muscle activation of the athlete's right and left quadriceps (e.g., whether one quadriceps is activated slower than the other quadriceps when jumping).

FIG. 5D is a user interface 535 showing exercise set score feedback according to one embodiment. In particular, the user interface 535 shows the set score 540 of "8.5" generated by the biofeedback module 410. In one embodiment, the set score 540 is point value out of a total possible 10 points, where a greater point value corresponds to a higher quality performance. If the athlete's metric for balance was satisfactory, then the set score 540 would be a greater point value, e.g., "9" or "10."

Figure 5E:
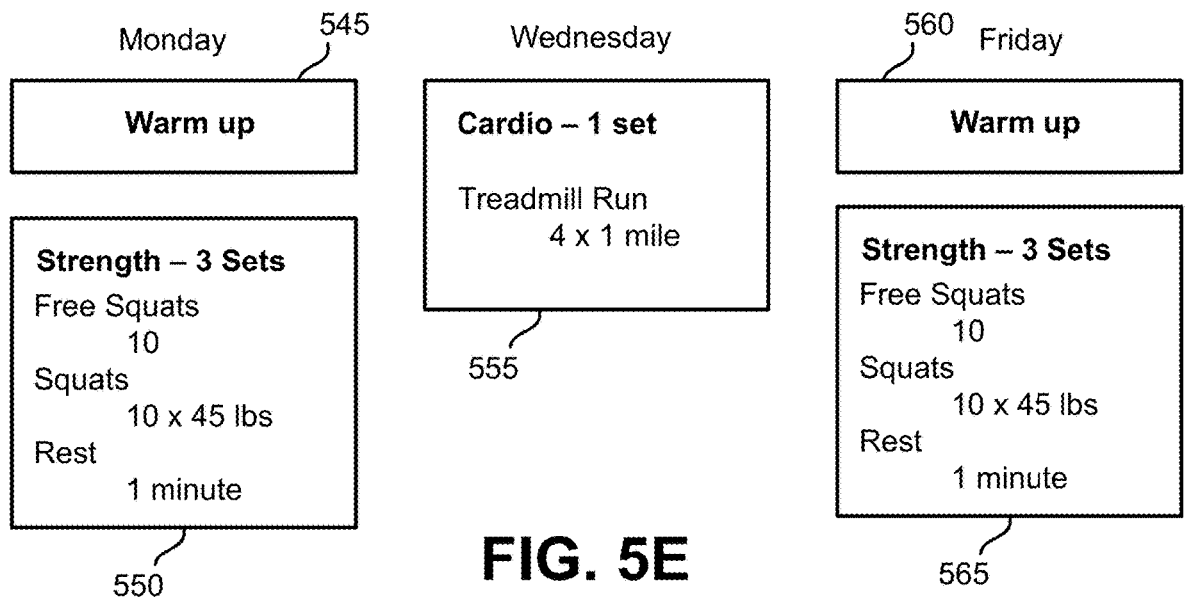
FIG. 5E is a user interface showing an exercise training program according to one embodiment.

FIG. 5E is a user interface showing an exercise training program according to one embodiment. The exercise program builder 430 generates the exercise training program for an athlete, e.g., the athlete 150 shown in FIG. 5A performing squats, and includes workouts scheduled on a Monday, Wednesday, and Friday of given week. On Monday, the exercise training program includes a warm up workout 545 and a strength workout 550. On Wednesday, the exercise training program includes a cardio workout 555. On Friday, the exercise training program includes a warm up workout 560 and a strength workout 565. The strength workouts 550 and 565 each include three sets of free squat exercises and squat exercises. Each set also include 1 minute of rest time. The free squat exercise has ten repetitions, and the squats exercise has ten repetitions with 45 pounds (e.g., weight on a barbell during each squat) per repetition. The cardio workout 555 has one set of four repetitions of a treadmill run exercise for 1 mile per repetition.

Figure 5F:
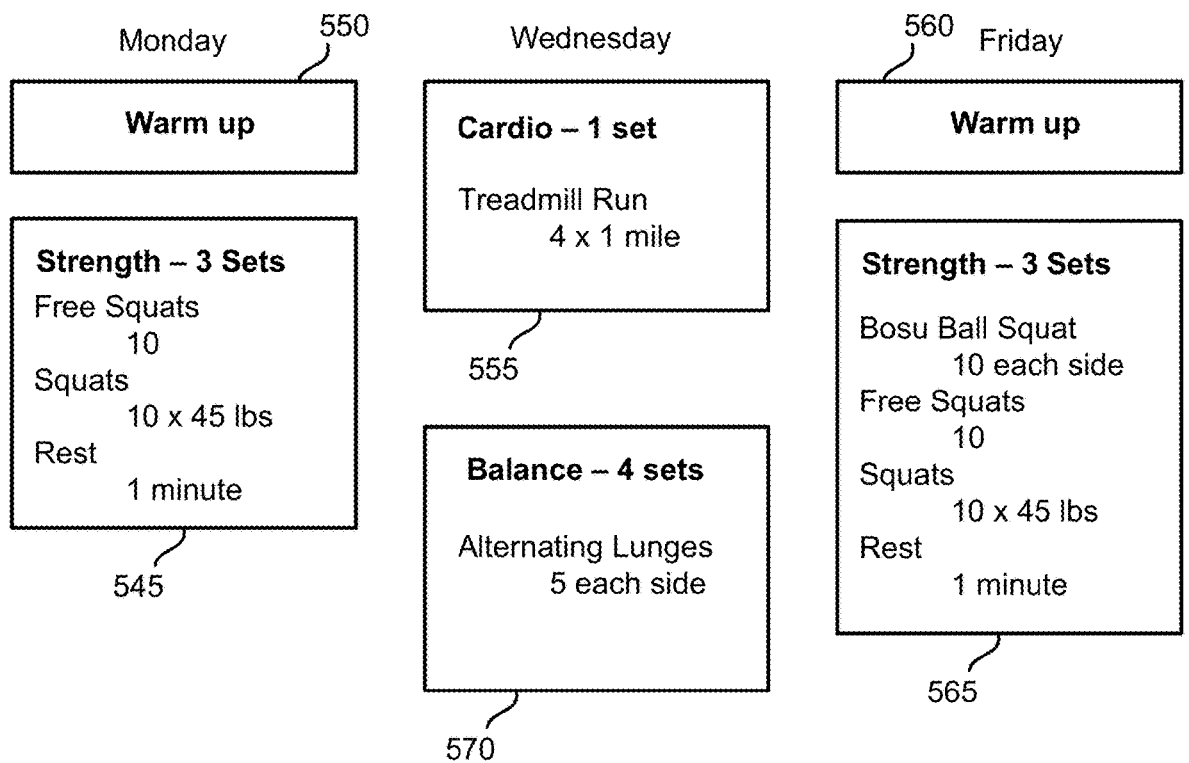
FIG. 5F is a user interface showing a modified version of the exercise training program shown in FIG. 5E according to one embodiment.

FIG. 5F is a user interface showing a modified version of the exercise training program shown in FIG. 5E according to one embodiment. Compared to the exercise training program shown in FIG. 5E, the modified version has an additional balance workout 570 scheduled on Wednesday and a modified strength workout 565 scheduled on Friday. The balance workout 570 includes four sets of alternating lunges. The alternating lunge exercise is a unilateral exercise focusing on each of the left and right sides separately. This unilateral exercise allows the athlete to train the athlete's left quad, independently of the right quad, to strengthen the left quad muscle rather than completing bilateral exercises such as squats where the athlete may be biased toward one side of muscles over the other side. The alternating lunge exercise has five repetitions per side per set. The modified strength workout 565 includes an additional single leg squat BOSU® ball exercise with ten repetitions per side (e.g., right leg and left leg).

The exercise program builder 430 generates the modified version of the exercise training program for the athlete 150 performing squats based on metrics of performance by the athlete 150. For example, as shown in the user interfaces in FIGS. 5B-D, the athlete 150 has an unsatisfactory metric for balance. Thus, the exercise program builder 430 automatically modifies (e.g., without requiring user input) the original exercise training program shown in FIG. 5E by adding exercises that help develop the athlete's balance in the lower body, specifically, the alternating lunges and the single leg squat BOSU® ball exercise.

VI. Example Use Case: Bench Press

Figure 6A:
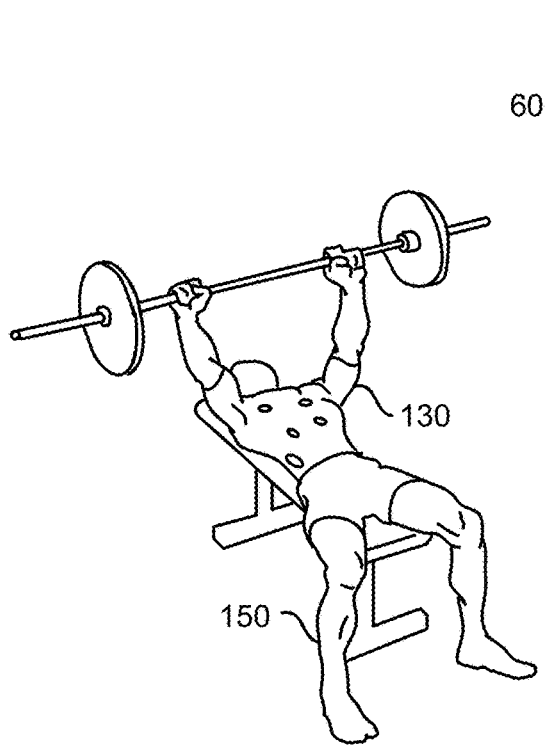
FIG. 6A is a diagram of an athlete performing a bench press exercise while wearing a sensor-equipped garment according to one embodiment.
Figure 6B:
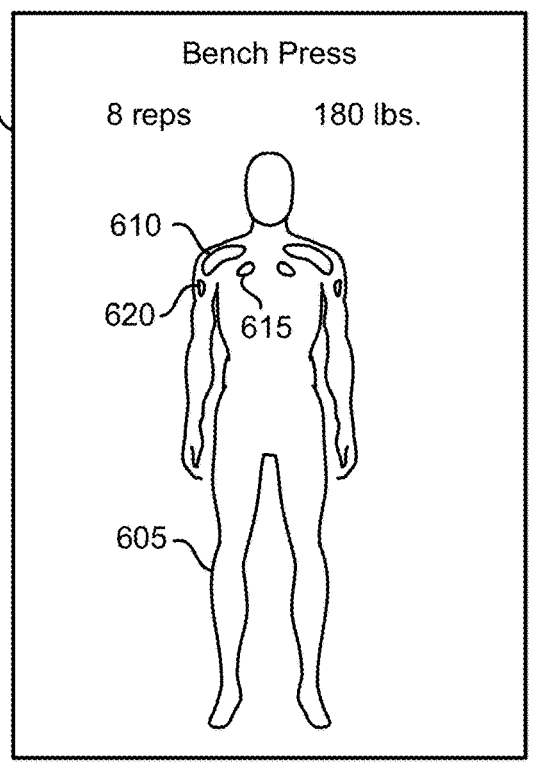
FIG. 6B is a user interface showing muscle activation feedback according to one embodiment.
Figure 6C:
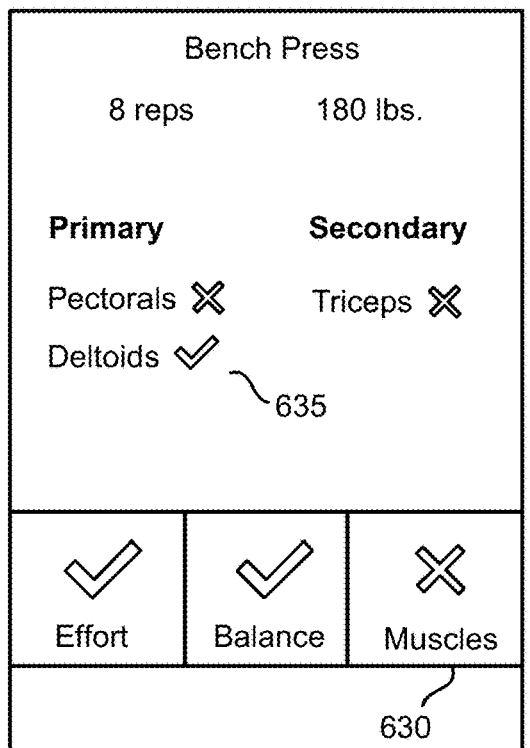
FIG. 6C is a user interface showing target muscle feedback according to one embodiment.
Figure 6D:
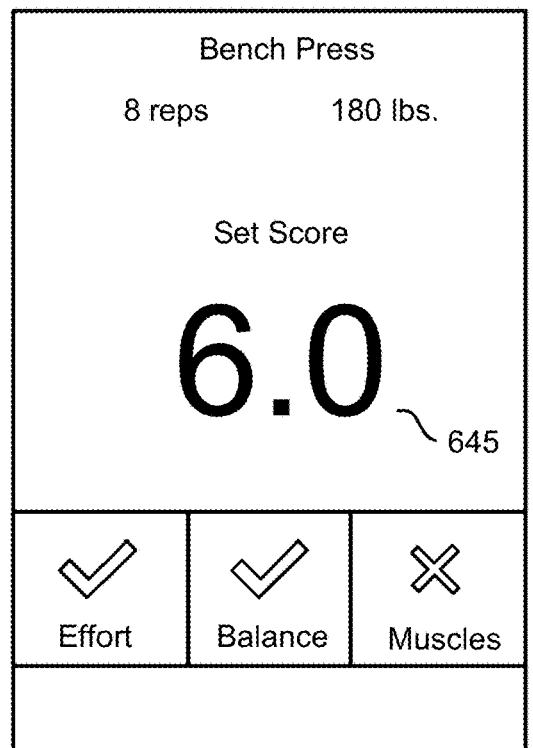
FIG. 6D is a user interface showing exercise set score feedback according to one embodiment.

FIG. 6A is a diagram of an athlete 150 performing a bench press exercise while wearing a sensor-equipped garment 130 according to one embodiment. The athlete 150 is wearing the athletic garment 130 which is a shirt including sensors that generate muscle activation data about the athlete's upper body muscles, e.g., pectorals, deltoids, and triceps. The athlete 150 performs a set of the bench press exercise with a barbell, e.g., a set of eight repetitions with 180 pounds of weight on the barbell per repetition. FIGS. 6B-D show user interfaces generated by the interface manager 460 in real time while the athlete 150 performs the bench press exercise.

FIG. 6B is a user interface 600 showing muscle activation feedback according to one embodiment. The muscle activation feedback is represented by a depiction of muscles overlaid on an image 605 of the athlete 150. In particular, the image 605 shows a metric for the athlete's right deltoids 610, right pectorals 615, and right triceps 620. The depiction of the right deltoids 610 is larger than those of the right pectorals 615 and right triceps 620 because the athlete is using a higher contribution of the right deltoid compared to the chest or triceps to complete a movement of an exercise.

FIG. 6C is a user interface 625 showing target muscle feedback according to one embodiment. The user interface 625 shows a depiction, e.g., based on biofeedback generated by the biofeedback module 410, of three categories 630 of exercise feedback: effort, balance, and muscles. The categories 630 shown in FIG. 6C indicate that the athlete 150 has a satisfactory metric for effort and balance, but not for muscles (also referred to as target muscles). The target muscles has an unsatisfactory metric, e.g., because the athlete 150 is focusing on using the incorrect types of muscles for the bench press exercise. In particular, the checkmark and X marks in the depiction of target muscles 635 indicate that the athlete is using the deltoid muscles more than the pectorals and triceps.

FIG. 6D is a user interface 640 showing exercise set score feedback according to one embodiment. In particular, the user interface 640 shows the set score 645 of "6.0" generated by the biofeedback module 410. If the athlete's metric for target muscles was satisfactory, then the set score 645 would be a greater value.

FIG. 6E is a user interface showing an exercise training program according to one embodiment. The exercise program builder 430 generates the exercise training program for an athlete, e.g., the athlete 150 shown in FIG. 6A performing bench presses, and includes workouts scheduled over two weeks. On the first week, the exercise training program includes a strength workout 650 on Monday and a strength workout 655 on Friday. On the Monday of the second week, the exercise training program includes a strength workout 660. The strength workouts each include three sets of bench press exercises and 1 minute of rest time. The number of repetitions per set of bench press exercises is eight for each of the three strength workouts, though the weight gradually increases. Specifically, the weights in strength workouts 650, 655, and 660 are 180 pounds, 190 pounds, and 200 pounds, respectively.

FIG. 6F is a user interface showing a modified version of the exercise training program shown in FIG. 6E according to one embodiment. Compared to the exercise training program shown in FIG. 6E, the modified version has an additional strength workout 665 scheduled on Wednesday of the first week and another additional strength workout 670 scheduled on Friday of the second week. The strength workout 665 includes three sets of overhead press exercises and 1 minute of rest. Each set of overhead press exercises has five repetitions of 85 pounds. The strength workout 670 is substantially the same as the strength workouts 650, 655, and 660, but with a different weight. The weights for the sets of bench press exercises are lower relative to those shown in FIG. 6E. Specifically, the weights in strength workouts 655, 660, and 670 are 150 pounds, 160 pounds, and 170 pounds, respectively.

The exercise program builder 430 generates the modified version of the exercise training program for the athlete 150 performing bench presses based on metrics of performance by the athlete 150. For example, as shown in the user interfaces in FIGS. 6B-D, the athlete 150 has an unsatisfactory metric for target muscles. In particular, the athlete 150 has weak deltoid muscles, so the athlete's deltoids are over exerted when the athlete performs the bench press exercise. Thus, the exercise program builder 430 automatically modifies (e.g., without requiring user input) the original exercise training program shown in FIG. 6E by adding exercises (e.g., overhead press exercises) that help develop the athlete's deltoid muscle strength. Further, the exercise program builder 430 modifies the existing strength exercises by reducing the amount of weight per bench press exercise. Adjusting the amount of weight to a suitable level for the athlete 150 helps the athlete exercise without under-exerting or over-exerting beyond the athlete's capabilities.

VII. Example Process Flows

FIG. 7 is a flowchart of a process 700 for providing exercise feedback according to one embodiment. In some embodiments, the process 700 is performed by the exercise feedback system 100—e.g., modules of the exercise feedback system 100 described with reference to FIG. 4A—within the system environment in FIG. 1. The process 700 may include different or additional steps than those described in conjunction with FIG. 7 in some embodiments or perform steps in different orders than the order described in conjunction with FIG. 7.

The exercise feedback system 100 receives 710 physiological data from a garment worn by a user, e.g., the athlete 150 wearing garment 130 shown in FIG. 5A, while performing an exercise, e.g., squats. The physiological data is generated by sensors of the garment (e.g., sensors 210-280 shown in FIG. 2) and can describe muscle activation data of particular muscles of the user, heart rate data, or other types of data such as motion data. The biofeedback module 410 compares 720 the physiological data to reference data selected based on the exercise. For example, the reference data includes a target muscle data or a baseline motion profile for squat exercises. The reference data can also be based on previously generated physiological data of the user, e.g., during exercises that the user performed in the past. The biofeedback module 410 generates 730 biofeedback based on the comparison. The biofeedback may indicate a metric of performance of the exercise by the user, e.g., whether the user performed the exercise with a satisfactory level of effort or balance, or using the proper form or target muscles. The exercise feedback system 100 provides 740 the biofeedback to a mobile device of the user, e.g., the athlete's device 110 shown in FIG. 1. The biofeedback is displayed on a graphical user interface to the user. The graphical user interface can include a depiction of the particular muscles of the user, e.g., the depiction of the right quadriceps 510 and left quadriceps 520 in the user interface 500 shown in FIG. 5B. In other embodiments, the athlete's device 110 communicates the metric of performance of the user in other suitable formats, e.g., as an audio feedback via speakers of the athlete's device 110, or visual feedback including text presented on a display screen of the athlete's device 110.

Figure 8:
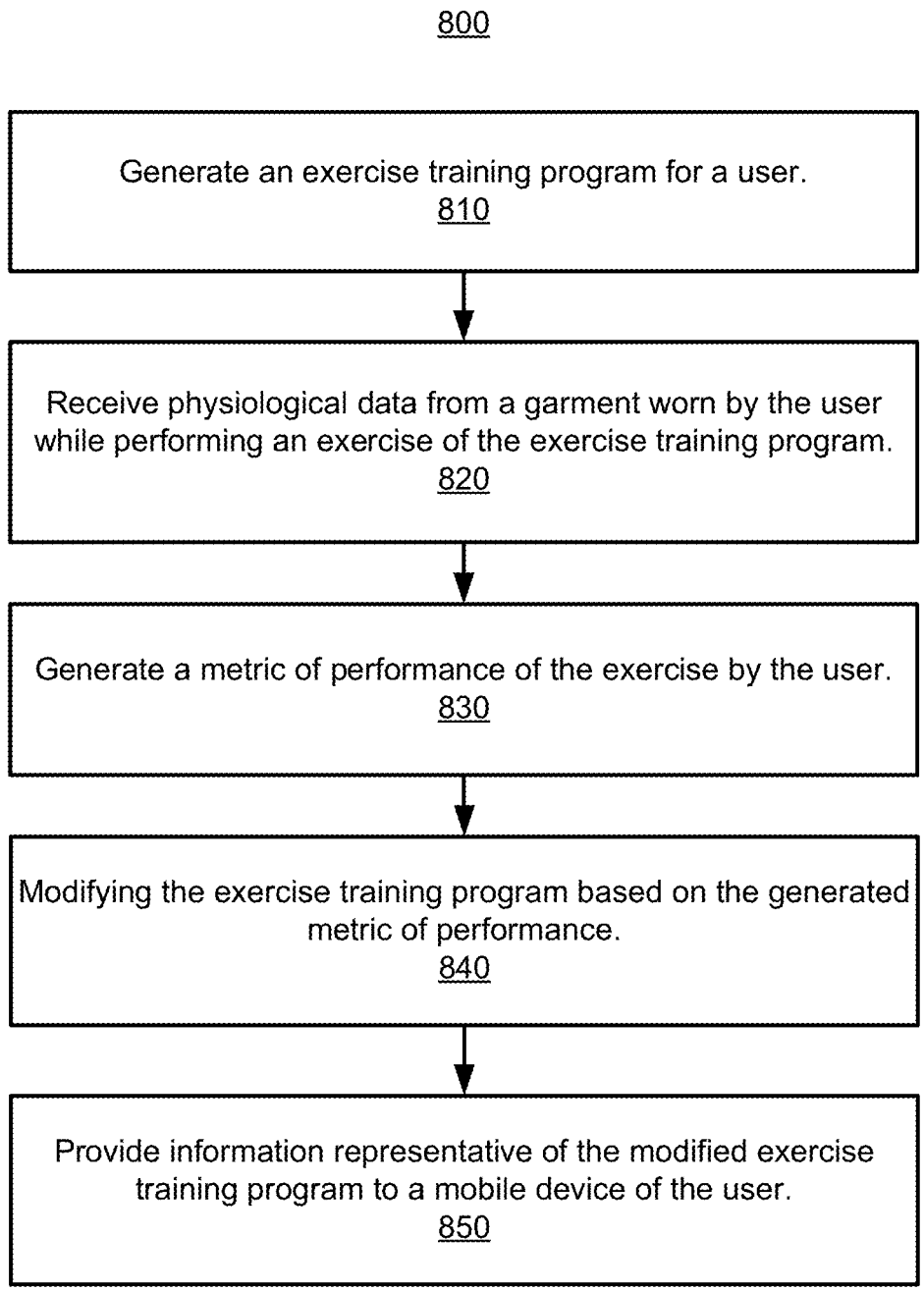
FIG. 8 is a flowchart of a process for modifying an exercise training program according to one embodiment.

FIG. 8 is a flowchart of a process 800 for modifying an exercise training program according to one embodiment. In some embodiments, the process 800 is used by the exercise feedback system 100—e.g., modules of the exercise feedback system 100 described with reference to FIG. 4A—within the system environment in FIG. 1. The process 800 may include different or additional steps than those described in conjunction with FIG. 8 in some embodiments or perform steps in different orders than the order described in conjunction with FIG. 8.

The exercise program builder 430 generates 810 an exercise training program for a user, e.g., the athlete 150 shown in FIG. 6A. The exercise feedback system 100 receives 820 physiological data from a garment worn by the user while performing an exercise of the exercise training program, e.g., the bench press exercise of a workout of the exercise training program shown in FIG. 6E. The biofeedback module 410 generates 830 a metric of performance of the exercise by the user. For example, the metric of performance indicates that the user is not using all of the target muscles for the bench press exercise, as shown in FIG. 6C. The exercise program builder 430 modifies 840 the exercise training program based on the generated metric of performance. For example, the exercise program builder 430 modifies the exercise training program shown in FIG. 6E, which to help the athlete train to use all of the target muscles for bench press exercises. The exercise feedback system 100 provides 850 information representative of the modified exercise training program (e.g., the user interface shown in FIG. 6F) to a mobile device (e.g., the athlete's device 110 shown in FIG. 1) for display to the user. To improve the efficiency of exercise training, it is important for the athlete to understand whether the athlete is gaining the intended training adaptation from the exercise or training program (e.g., improving power, strength, hypertrophy, endurance, speed, etc.)

VIII. Additional Example User Interfaces

Figure 9A:
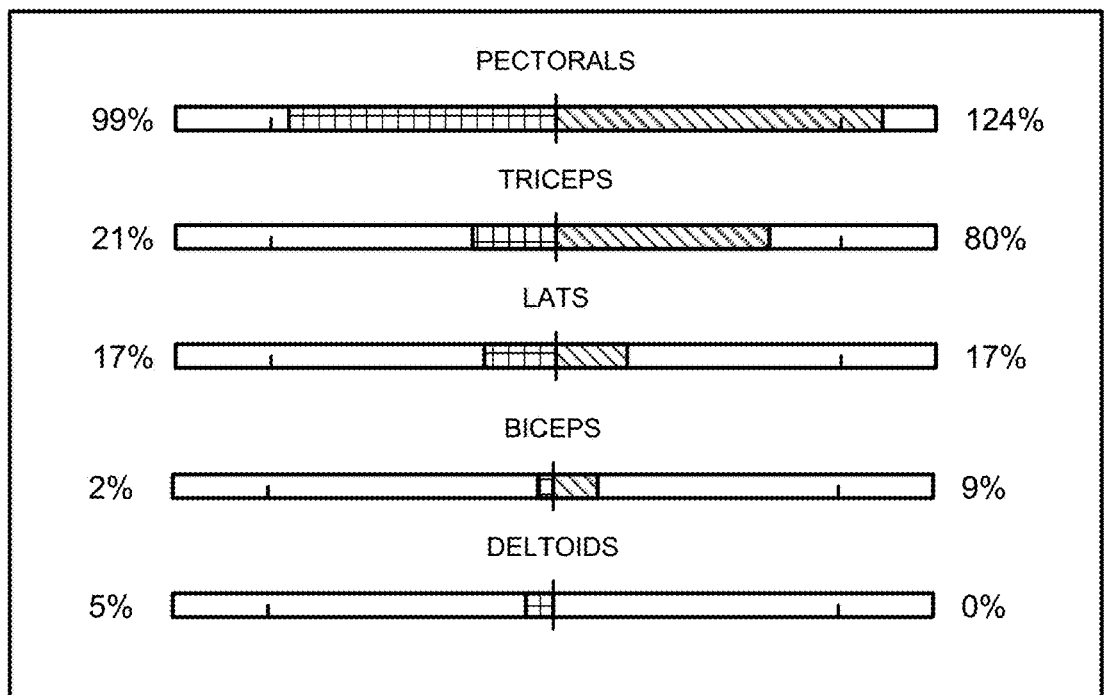
FIG. 9A is a user interface showing muscle activation feedback for upper body muscles according to one embodiment.

FIG. 9A is a user interface 900 showing muscle activation feedback for upper body muscles according to one embodiment. The user interface 900 shows the peak muscle activation (e.g., based on the amplitude of physiological data generated by sensors) for a set of muscles during a particular set completed by an athlete. For instance, the peak muscle activations for the left and right pectorals are 99% and 124%, respectively. In some embodiments, the peak muscle activation may be a percentage greater than 100% because the percentage is relative to a baseline calibration value for the corresponding muscle. In some embodiments, the peak muscle activation is greater when the athlete is performing exercises with power movements, e.g., lifting heavy weights at a high velocity.

Figure 9B:
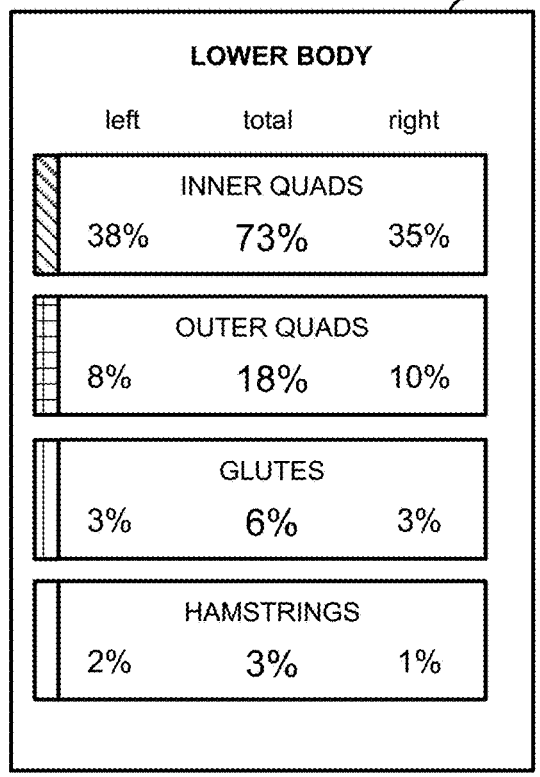
FIG. 9B is a user interface showing muscle activation feedback for lower body muscles according to one embodiment.

FIG. 9B is a user interface 910 showing muscle activation feedback for lower body muscles according to one embodiment. The user interface 910 indicates that the muscle contributions for the inner quads, outer quads, glutes, and hamstrings are 73%, 18%, 6%, and 3%, respectively. The biofeedback module 410 determines the muscle contributions based on the work (i.e., energy expenditure) of the muscles over a period of time (e.g., corresponding to a set of an exercise). In one embodiment, the biofeedback module 410 determines the muscle contributions based on the ratio of work for a given muscle to the total accumulated work for a set of muscles (e.g., the lower body muscles: inner quads, outer quads, glutes, and hamstrings). The user interface 910 also indicates the muscle contributions distributed between the left and right sides of each muscle.

Figure 9C:
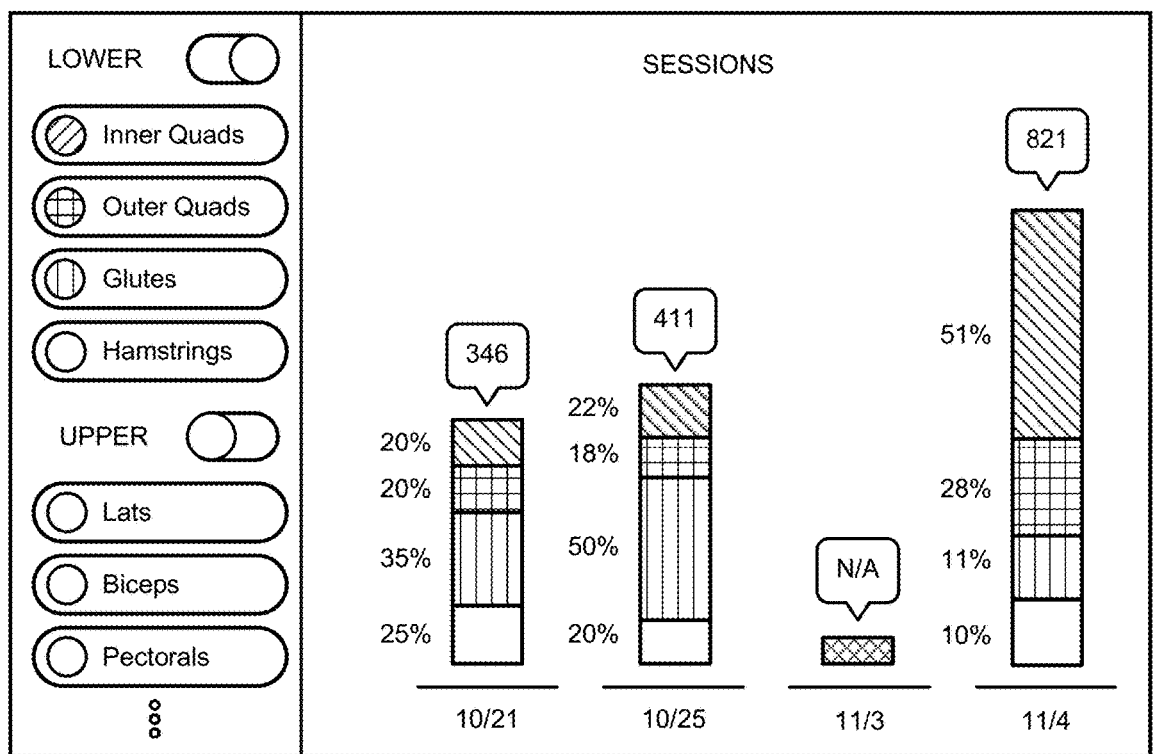
FIG. 9C is another user interface showing muscle activation feedback for lower body muscles according to one embodiment.

FIG. 9C is another user interface 920 showing muscle activation feedback for lower body muscles according to one embodiment. The user interface 920 indicates that the total work exerted by the athlete's muscles during training sessions on Oct. 21, Oct. 25, Nov. 3, and Nov. 4 are 346, 411, N/A (athlete did not complete a training session that day), and 821. The height of each bar in the graph is proportional to the total work for the corresponding session. The user interface 920 also indicates percentages representing the contribution of each muscle in the group of lower body muscles shown in FIG. 9C to the total work. For instance, the contribution for the inner quads, outer quads, glutes, and hamstrings are 51%, 28%, 11%, and 10%, respectively, for the session on Nov. 4.

Figure 9D:
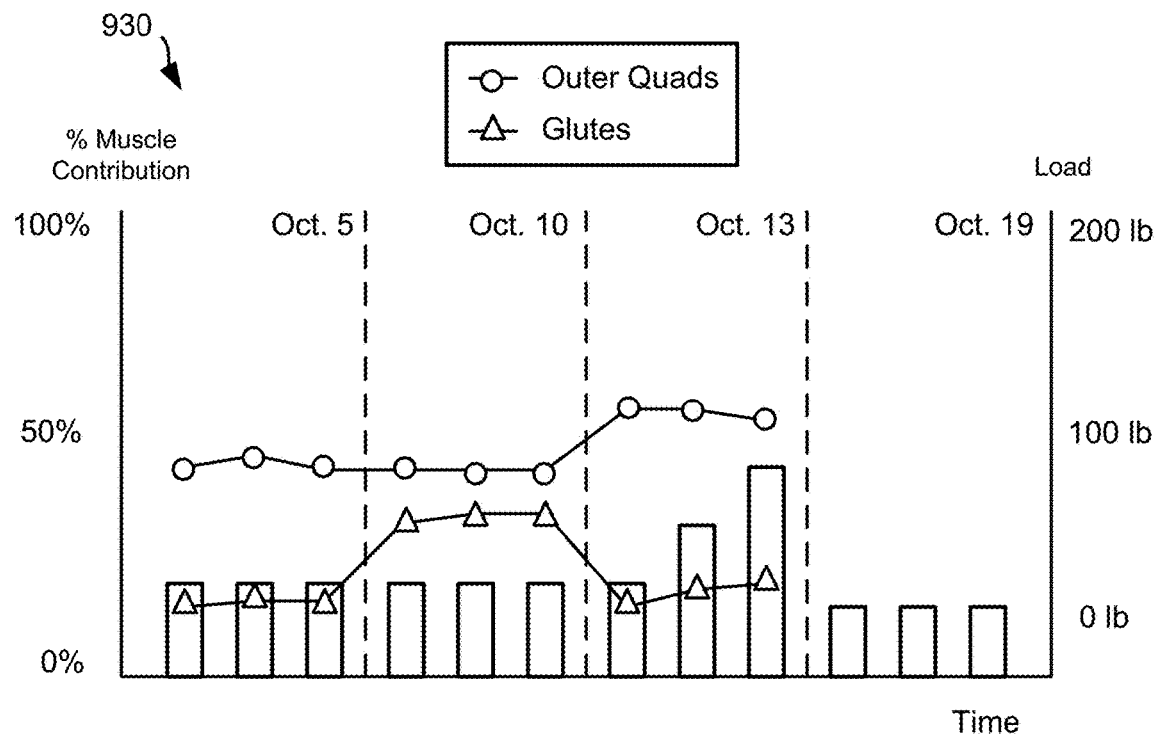
FIG. 9D is a user interface showing muscle contribution over time according to one embodiment.

FIG. 9D is a user interface 930 showing muscle contribution over time according to one embodiment. In particular, the user interface 930 shows a bar graph and lines graphs on the same time axis. The bar graph indicates how much weight an athlete lifted for each set of an exercise on a given day (e.g., session). For instance, during the session of Oct. 5, the athlete performed three sets of a squat exercise with 30 pounds for each set. The overlaying line graphs indicate the percentage muscle contributions for the outer quads and the glutes, according to the legend of the graph. In one example use case, the outer quad muscle contribution increases and the glutes muscle contribution decreases when the athlete performs sets of squat exercises using greater weights, as shown in the section of the graph corresponding to the session on Oct. 13. The changes in muscle contributions may help show a breakdown of proper squat exercise form at greater weights because the athlete is compensating for weaker glutes by exerting more energy using the outer quads. The muscle contributions may also change as result of the athlete's fatigue over time. Thus, the athlete or a coach may use the biofeedback shown in the user interface 930 to modify future workouts, e.g., by reducing the weights for squats.

IX. Additional Considerations

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method comprising:
receiving physiological data from a garment worn by a user, the physiological data describing muscle activation of a plurality of muscles of the user while performing an activity, the garment comprising a plurality of sensors configured to generate the physiological data;
determining a target muscle profile associated with the activity, the target muscle profile derived from reference data from at least one reference entity performing the activity;
determining, from the physiological data for the user and over a period of time:
a first muscle contribution derived from a first accumulation of activation of a first muscle of the target muscle profile, and
a second muscle contribution derived from a second accumulation of activation of a second muscle of the target muscle profile;
determining a set of timestamps associated with phases of the activity based on times of activation of the first muscle and the second muscle;
generating biofeedback responsive to analyzing the second muscle contribution and the first muscle contribution with respect to the target muscle profile and the set of timestamps; and
providing the biofeedback to a client device of the user.

2. The method of claim 1, wherein the first muscle corresponds to a first muscle type, and the second muscle corresponds to a second muscle type.

3. The method of claim 2, wherein the first muscle type comprises an extensor muscle type, and wherein the second muscle type comprises a flexor muscle type.

4. The method of claim 2, wherein the first muscle type and the second muscle type comprise contralateral muscles.

5. The method of claim 1, further comprising determining a percentage contribution of the first muscle to the activity based upon a ratio of the first accumulation of activity for the first muscle to a total accumulation determined across all muscles of the target muscle profile.

6. The method of claim 1, further comprising determining a time difference between a first muscle activation associated with the first muscle contribution and a second muscle activation associated with the second muscle contribution.

7. The method of claim 6, wherein generating biofeedback further comprises determining usage of a correct sequence of muscles for an exercise type corresponding to the target muscle profile, based upon the time difference between the first muscle activation and the second muscle activation.

8. The method of claim 1, wherein the activity is a weight lifting exercise, and wherein a duration of time of the activity corresponds to at least one of a repetition and a set of the weight lifting exercise.

9. The method of claim 1, further comprising determining that the user deviated from proper form while performing the activity responsive to determining that the second muscle contribution is greater than the first muscle contribution.

10. The method of claim 1, wherein generating the biofeedback further comprises returning a performance trend over time based upon the physiological data of the user generated from previous performances of the activity by the user.

11. The method of claim 1, wherein generating the biofeedback comprises returning an analysis of level of effort of the user performing the activity, balance associated with muscle contributions of muscles of the target muscle profile for the activity, and an indication of performance of the user relative to a target range of performance for the activity.

12. The method of claim 1, wherein providing the biofeedback to the client device of the user comprises, for each phase of the activity, rendering an updated depiction of muscle contribution progress toward a target contribution of the target muscle profile, for at least one of the first muscle and the second muscle.

13. A system comprising a non-transitory computer readable storage medium having instructions encoded thereon that, when executed by a processor, cause the processor to:
  receive physiological data from a garment worn by a user, the physiological data describing muscle activation of a plurality of muscles of the user while performing an activity;
  determine a target muscle profile associated with the activity, the target muscle profile derived from reference data from at least one reference entity performing the activity;
  determine, from the physiological data for the user and over a period of time:
    a first muscle contribution derived from a first accumulation of activation of a first muscle of the target muscle profile, and
    a second muscle contribution derived from a second accumulation of activation of a second muscle of the target muscle profile;
  determine a set of timestamps associated with phases of the activity based on times of activation of the first muscle and the second muscle;
  generate biofeedback responsive to analyzing the second muscle contribution and the first muscle contribution with respect to the target muscle profile and the set of timestamps; and
  provide the biofeedback to a client device of the user.

14. The system of claim 13, further comprising the garment, the garment comprising a plurality of sensors configured to generate the physiological data.

15. The system of claim 13, further comprising instructions encoded thereon that, when executed by the processor, cause the processor to:
  compare the physiological data to reference data, wherein the reference data is based on previously obtained physiological data of a reference athlete, and wherein the biofeedback further indicates a comparison of a metric of performance of the activity by the user with an aggregate metric of performance of the exercise by the reference athlete.

16. The system of claim 13, further comprising instructions encoded thereon that, when executed by the processor, cause the processor to determine a percentage contribution of the first muscle to the activity based upon a ratio of the first accumulation of activity for the first muscle to a total accumulation determined across all muscles of the target muscle profile.

17. The system of claim 13, further comprising instructions encoded thereon that, when executed by the processor, cause the processor to determine a time difference between a first muscle activation associated with the first muscle contribution and a second muscle activation associated with the second muscle contribution.

18. The system of claim 17, further comprising instructions encoded thereon that, when executed by the processor, cause the processor to determine usage of a correct sequence of muscles for an exercise type corresponding to the target muscle profile, based upon the time difference between the first muscle activation and the second muscle activation.

19. The system of claim 13, further comprising instructions encoded thereon that, when executed by the processor, cause the processor to return a performance trend over time based upon the physiological data of the user generated from previous performances of the activity by the user.

20. The system of claim 13, further comprising instructions encoded thereon that, when executed by the processor, cause the processor to:
  receive motion data from the garment worn by a user; and
  determine that the user deviated from proper form while performing the activity responsive to (i) determining that the second muscle contribution is greater than the first muscle contribution and (ii) determining that the user deviated from a motion profile associated with the motion data.

* * * * *